(12) United States Patent
Matzinger et al.

(10) Patent No.: US 6,680,176 B2
(45) Date of Patent: Jan. 20, 2004

(54) IDENTIFICATION OF CANDIDATE LIGANDS WHICH MODULATE ANTIGEN PRESENTING CELLS

(75) Inventors: Polly Matzinger, Bethesda, MD (US); John Paul Ridge, Gaithersburg, MD (US)

(73) Assignee: The United States of America, as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/313,487

(22) Filed: May 17, 1999

(65) Prior Publication Data

US 2003/0170236 A1 Sep. 11, 2003

(51) Int. Cl.⁷ .................. G01N 33/53; G01N 33/555; G01N 33/567; G01N 33/537; G01N 33/543
(52) U.S. Cl. .................. 435/7.24; 435/325; 435/375; 435/377; 435/343; 435/7.92; 436/536
(58) Field of Search ................. 435/325, 375, 435/377, 7.24, 7.92, 343; 436/536

(56) References Cited

U.S. PATENT DOCUMENTS

| | | |
|---|---|---|
| 4,612,337 A | 9/1986 | Fox, Jr. et al. |
| 4,657,760 A | 4/1987 | Kung et al. |
| 4,818,540 A | 4/1989 | Chien et al. |
| 5,093,115 A | 3/1992 | Stevenson |
| 5,206,344 A | 4/1993 | Katre et al. |
| 5,225,212 A | 7/1993 | Martin et al. |
| 2003/0022860 A1 | 1/2003 | Melief et al. |

FOREIGN PATENT DOCUMENTS

WO 99/61065 12/1999

OTHER PUBLICATIONS

Curtsinger et al. J. Immunol. Methods 209:47–57, 1997.*
Ahmed, R. et al. *J. Virol.* 62:2102–2106 (1988). "T4+ Helper Cell Function in Vivo: Differential Requirement for Induction of Antiviral Cytotoxic T–Cell and Antibody Responses".
Altschul et al, *J. Mol. Biol.* 215:403 (1990). "Basic Local Alignment Search Tool".
Anderson, A.O. & Shaw, S., *Semin. Immunol.* 5:271–282 (1993), "T cell adhesion to endothelium: the FRC conduit system and other anatomic and molecular features which facilitate the adhesion cascade in lymph node".
Armstrong et al. *J. Infectious Diseases* 171:1042–1045 (1995), "A Phase I Study of Chemically Synthesized Verotoxin (Shiga–like toxin) Pk–Trisaccharide Receptors attached to Chromosorb for Preventing Hemolytic–Uremic Syndrome".

Auchincloss, H., Jr. et al. *Proc. Natl. Acad. Sci. U.S.A.* 90:3373–3377 (1993), "The role of indirect recognition in initiating rejection of skin grafts from major histocompatibility complex class II–deficient mice".
Bennett et al., *Nature*, 186:65–70 (1997), "Help for cytotoxic–T–cell responses is mediated by CD40 signalling."
Bevan, M.J., *J. Exp. Med.* 143;1283–1288 (1976), "Cross–priming for a secondary cytotoxic response to minor h antigens with H–2 congenic cells which do not cross–react in the cytotoxic assay".
Boog, C.J. et al., *Nature* 318:59–62 (1985), "Abolition of specific immune response defect by immunization with dentritic cells".
Buller, R.M. et al., *Nature* 328:77–79 (1987), "Induction of cytotoxic T–cell responses in vivo in the absence of CD4 helper cells".
Cardin, R.D. et al., *J. Exp. Med.* 184:863–871 (1996), "Progressive Loss of CD8+ T Cell–mediated control of a y–Herpesvirus in the Absence of CD4+ T Cells".
Caux, C. et al., *J. Exp. Med.* 180:1263–1272 (1994), "Activation of Human Dendritic Cells through CD40 Cross–linking".
Cella et al., *J. Exp. Med.* 184: 747–752 (1996), "Ligation of CD40 on Dendritic Cells Triggers Production of High Levels of Interleukin–12 and Enhances T Cell Stimulatory Capacity: T–T Help via APC Activation".
Chen et al., *Science* 265:1237–1240 (1994), "Regulatory T Cell Clones Induced by Oral Tolerance: Suppression of Autoimmune Encephalomyelitis".
Croft, M. et al., *J. Immunol.* 152:2675–2685 (1997), "Naive Versus Memory CD4 T Cell Response to Antigen".
Erickson et al., *Science* 249:527–533 (1990), "Design, Activity, and 28 A Crystal Structure of a $C_2$ Symmetric Inhibitor Complexed to HIV–1 Protease".
Feeney, A.J. et al., *J. Mol. Cell Immunol.* 1:211–222 (1984), "T Helper Cells Required for the in vitro Primary Antibody Response to SRBC are neither SRBC–Specific nor MHC–Restricted".
Fetrow and Skolnick, *J. Mol. Biol.* 281:949–968 (1998), "Method for Prediction Function from Sequence using the Sequence–to–Structure–to–Function Paradigm with application to Glutaredoxins/Thioredoxins and $T_1$ Ribonucleases".

(List continued on next page.)

Primary Examiner—Gerald R. Ewoldt
(74) Attorney, Agent, or Firm—Knobbe, Martens, Olson & Bear LLP

(57) ABSTRACT

The present invention relates to the identification of candidate ligands which modulate antigen presenting cells. Specifically, ligands which superactivate antigen presenting cells are identified.

6 Claims, 5 Drawing Sheets

OTHER PUBLICATIONS

Fetrow et al., *J. Mol. Biol.* 282:703–711 (1998), "Functional Analysis of the *Escherichia coli* Genome using the Sequence–to–Structure–to–Function paradigm: Identification of Proteins Exhibiting the Glutaredoxin/Thioredoxin Disulfide Oxidoreductase Activity".

Foy, T.M. et al., *Semin. Immunol.* 6:259–266 (1994), "The expansive role of CD40 and its ligand, gp39, in immunity".

Fuchs, E.J. & Matzinger, P., *Science* 258:1156–1159 (1992), "B Cells Turn Off Virgin But Not Memory T Cells".

Gilboa et al., *Cancer Immunol. And Immunoth.* 46:82–87 (1998), "Immunotherapy of cancer with dendritic–cell–based vaccines".

Gray, D. & Matzinger, P., *J. Exp. Med.* 174:969–974 (1991), "T Cell Memory is short–lived in the absence of antigen".

Guerder and Matzinger, *Cold Spring Harbor Symposia on Quantitative Biology*, vol. 54:799–805 (1989), "Activation versus Tolerance: A Decision Made by T Helper Cells."

Guerder, S. & Matzinger, P., *J. Exp. Med.* 176:553–564 (1992), "A Fail–Safe Mechanism for Maintaining Self–Tolerance."

Hodgson, *Bio. Technology* 9:19–21 (1991), "Data–directed drug design".

Hou, S. et al., *J. Virol.* 69:1429–1434 (1995), "Host response to sendai virsu in mice lacking Class II major histocompatibility complex glycoproteins".

Inaba, K.. et al., *J. Exp. Med.* 166:182–194 (1987), "Direct activation of CD8+ cytotoxic T lymphocytes by dendritic cells".

Janeway, C.A., Jr., *Cold Spring Harb. Symp. Quant. Biol.* 54 Pt 1:1–13 (1989), "Approaching the asymptote? evolution and revolution in immunology".

Katona et al., *J. Immunol.* 146:4215–4221 (1991), "IL–4 requirements for the generation of secondary in vivo IgE responses[1]".

Keene, J.A. & Forman, J., *J. Exp. Med.* 155:768–782 (1982), "Helper activity is required for the in vivo generation of cytotoxic T lymphocytes".

Kennedy et al., *J. Immuno.* 96:973–980 (1966), "The proliferative capacity of antigen–sensitive precursors of hemolytic plaque–forming cells".

Koch, F. et al., *J. Exp. Med.* 184:741–746 (1996), "High Level IL–12 production of murine dentritic cells upregulation via MHC Class I and CD40 molecules and downregulation by IL–4 and IL–10".

Lanzavecchia, A., *Nature* 314:537–539 (1985), "Antigen–specific interaction between T and B cells".

Leist, T.P. et al., *Scand. J. Immunol.* 30:679–686 (1989), "Impaired generation of anti–viral cytotoxicity against lymphocytic choriomeningitis and vaccinia virus in mice treated with CD–4 specific monoclonal antibody".

Linsley et al., *Science*, 257:792–795 (1992), "Immunosuppression in vivo by a soluble form of the CTLA–4 T cell activation molecule".

Liu, L. et al., *Adv. Exp. Med. Biol.* 417:375–381 (1997), "A potential pathway of TH2 development during primary immune response".

Liu, Y. et al., *J. Exp. Med.* 185:251–262 (1997), "Distinct costimulatory molecules are required for the induction of effector and memory cytotoxic lymphocytes", Matzinger, P., *Annu. Rev. Immunol.*, 12:991–1045 (1994), "Tolerance, Danger, and the Extended Family."

Mitchison, N.A. & O'Malley, C., *Eur. J. Immunol.* 171579–1583 (1987), "three–cell–type clusters of T cels with antigen–presenting cels best explain the epitope linkage and noncognate requirements of the in vivo cytolytic response".

Mueller, D.L. et al., *Ann. Rev. Immunol.* 7:45–480 (1989), "Conal expansion versus functional conal inactivation".

Paliard, X. et al., *J. Immunol.* 141:849–855 (1988), "Simulaneous production of IL–2, IL–4, and IFN–y by Activated Human CD4 and CD8p30 T Cell clones".

Pearson and Lipman, *Proc. Natl. Acad. Sci. USA*, 85:2444 (1988), "Improved tools for biological sequence comparison".

Rees, M.A. et al., *Proc. Natl. Acad. Sci. U.S.A.* 87:2765–2769 (1990), "In vivo induction of antigen–specific transplantation tolerance to $Qa1^a$ by exposure to alloantigen in the absence of T–cell help".

Ridge et al., *Nature*, 393:474–478 (1998), "A conditioned dendritic cell can be a temporal bridge between a $CD4^+$ T–helper and a T–killer cell."

Roopenian, D.C. et al., *J. Immunol.* 130:542–545 (1983), "Helper Cel–independent cytolotyic T lymphocytes specific for a minor histocompatibility antigen".

Rosenberg, A.S. et al., *Nature* 322:829–831 (1986), "Analysis of T–cell subsets in rejection of $K^b$ mutant skin allogrfts differing at class I MHC".

Saeland, et al., *J. Exp. Med.* 178:113–120 (1993), "Human B Cell precursors proliferate and express CD23 after CD40 ligation".

Sali and Blundell *J. Mol. Biol.* 234:2170241 (1997), Comparative protein modelling by satisfaction of spatial restraints.

Schoenberger et al., *Nature*, 393:480–483 (1998), "T–cell help for cytotoxic T lymphocytes is mediated by CD40–CD40L interactions."

Shimuzu, T. & Takeda, S., *Eur. J. Immunol.* 27:500–508 (1997), "CD8 T cells from major histocompatibility complex class II–deficient mice respond vigorously t class II molecules in a primary mixed lymphocyte reaction".

Simpson, E. & Gordon, R.D., *Immunol. Rev.* 35:59–75 (1977), "Responsiveness to HY antigen lr gene complementation and target cell specificity".

Stavnezer, *J. Immunol*, 155:1647–1651 (1995), "Regulation of antibody production and class switching by TGF–$\beta^1$".

Steinman, R.M., *Annu. Rev. Immunol.* 9271–296 (1991), "The dendritic cell system and its role in immunogenicity".

Tony, H.P. and Parker, D.C., *J. Exp. Med.* 161:223–241 (1985), "Major histocompatibility complex–restricted, polyclonal B cell responses resulting from helper T cell recognition of antiimmunoglobulin presented by small B lymphocytes".

Torseth, J.W. et al., *J. Infect. Dis.* 155:641–648 (1987), "β Interferon produced by keratinocytes in human cutaneous infection with herpes simplex virus".

Tripp, R.A., et al., *J. Immunol.* 155:2955–2959 (1995), "Characteristics of the influenza virus–specific CD8+ T cell response in mice homozygous for disruption of the $H-21A^b$ gene[1]".

Vann, D.C. and Dotson, D.R., *J. Immunol.* 112:1149–1157 (1974), "Cellular cooperation and stimulatory factors in antibody responses: limiting dilution analysis in vitro".

von Boehmer, H. et al., *Proc. Natl. Acad. Sci. U.S.A.* 75:2439–2442 (2978), "Major histocompatibility complex-linked immune-responsiveness is acquired by lymphocytes of low-responder mice differentiating in thymus of high-responder mice".

Wells, *Methods in Enzymol.*, 202:390–411 (1991), "Systematic Mutational analyses of protein–protein interfaces".

Wilbanks, G.A. & Streilien, J.W., *Eur. J. Immunol.* 22:1031–1036 (1992), "Fluids from immune privileged sites endow macrophages with the capacity to induce antigen-specific immune deviation via a mechanism involving transforming growth factor-β".

Wu, Y. & Liu, Y., *Curr. Biol.* 4:499–505 (1994), "Viral induction of co-stimulatory activity of antigen-presenting cells bypasses the need for CD4+ T-cell help in CD8+ T-cell responses".

Yang and Wilson, *Science* 273:1862–1864 (1996), "CD40 Ligand-dependent T cell activation: requirement of B7–CD28 signaling through CD40".

* cited by examiner a  Three-cell interaction b  Sequential two-cell interactions

IDENTIFICATION OF CANDIDATE LIGANDS WHICH MODULATE ANTIGEN PRESENTING CELLS

FIELD OF THE INVENTION

The present invention relates to the field of immunology. More specifically, novel biotechnological tools, therapeutics and phophylactics, which modulate antigen presenting cell activity are disclosed.

BACKGROUND OF THE INVENTION

The mature, circulating, antigen specific cells of the immune system face a challenge that does not trouble most other cells of the body. They must find each other, and they must do it often and quickly, every time there is need of an immune response. The problem is compounded by the rarity of the communicating partners, since only about 1 in $10^4$ circulating B lymphocytes can react to any particular antigen and the frequency of antigen specific T cells is thought to be similarly low. (Kennedy et al., *J. Immuno.* 96:973–980 (1966) and Vann, D. C. and Dotson, D. R., *J. Immunol.* 112:1149–1157 (1974)). Thus, a rare T helper cell specific for a particular pathogen needs to find an equally rare B cell specific for the same antigen. The fact that these encounters occur at all is due to the circulation patterns of these cells in lymph nodes and other specialized organs, as well as, the B cell's ability to act as an antigen presenting cell (APC) and attract the appropriate helper by creating a surface display of MHC class II molecules loaded with peptides from the antigen the B cell has captured. (Tony, H.P. and Parker, D. C., *J. Exp. Med.* 161:223–241 (1985) and Lanzavecchia, A., *Nature* 314:537–539 (1985)).

Once a B cell has attracted the right T helper cell, it uses a family of receptor-ligand pairs such as B7, CD40, and various cytokine receptors to stimulate the T cell and receive stimuli in turn. (Foy, T. M. et al., *Semin. Immunol.* 6:259–266 (1994)). T killer cells cannot do this and, if the two cell exchange between rare T and B cells seems challenging enough, the problem is far worse for communication between T helpers and T killer cells where the interaction requires a third participant, an APC, that brings the T helpers and T killers together by displaying antigens to both. (Keene, J. A. & Forman, J., *J. Exp. Med.* 155:768–782 (1982); Mitchison, N. A. & O'Malley, C., *Eur. J. Immunol.* 17:1579–1583 (1987); and Bennett, S. R. et al., *J. Exp. Med.* 186:65–70 (1997)).

The problem is two fold. First there is the challenge of bringing together three rare circulating cells. Second, since T killers do not express the sorts of co-stimulatory molecules expressed by B cells and APCs, (and, in mice, do not express MHC class II molecules with which to present antigen to helper T cells) the question of how help is stimulated and delivered remains.

Currently, investigators believe that dendritic cells exist in only two states: resting (an "immature" state) and activated (a "mature" state). In the activated state, a dendritic cell can present antigen and stimulate T helper cells, but not T killers. The successful priming of killer T cells is believed to require a three cell interaction between rare antigen loaded APCs and rare antigen specific helper T cells and killer T cells. In the model set forth by Keene and Forman, for example, the presenting cell has a rather passive relationship with the killer T cell and, like a B cell, the APC functions mainly to stimulate the helper cell, which then secretes cytokines necessary for the growth and activation of the neighboring killer T cell. (Keene, J. A. & Forman, J., *J. Exp. Med.* 155:768–782 (1982)).

For several reasons this picture is not completely satisfying. First, there is no guarantee that a rare T helper and an equally rare T killer should find the same APC at the same time. Because resting killers recognizing antigen become tolerant if there is no help available, many potentially useful killers would be rendered useless by the lack of immediate help. (Guerder, S. & Matzinger, P., *J. Exp. Med.* 176:553–564 (1992); Guerder, S. & Matzinger, P., *Cold Spring Harb. Symp. Quant. Biol.* 54:799 (1989); and Rees, M. A. et al., *Proc. Natl. Acad. Sci. U.S.A.* 87:2765–2769 (1990)). Second, the T helper would wastefully secrete its cytokines into an environment that may contain no killers to receive them. Third, killer responses to certain viruses are unimpaired by the absence of helper cells. (Tripp, R. A., et al., *J. Immunol.* 155:2955–2959 (1995); Buller, R. M. et al., *Nature* 328:77–79 (1987); Cardin, R. D. et al., *J. Exp. Med.* 184:863–871 (1996); Hou, S. et al., *J. Virol.* 69:1429–1434 (1995); Ahmed, R. et al. *J. Virol.* 62:2102–2106 (1988); and Leist, T. P. et al., *Scand. J. Immunol.* 30:679–686 (1989)). The three cell interaction model offers no explanation for the existence of these helper independent killer responses. In view of the foregoing and not withstanding the various efforts exemplified in the prior art, clearly several crucial pieces of the puzzle are missing.

BRIEF SUMMARY OF THE INVENTION

In the present invention, we demonstrate that an APC, preferably a dendritic cell, can be stimulated to a third state—a "superactivated" state. T helper cells, some viruses, and some antigens induce the dendritic cell to manifest the superactivated state. In contrast to activated dendritic cells, superactivated dendritic cells have the ability to activate a killer T cell by forming a two cell complex having the superactivated dendritic cell and the killer T cell. Notably, the superactivated APC activates a killer cell in the absence of a T helper cell. Additionally, we have discovered that specific agents which interact with the APC superactivate the APC or block, inhibit, or prevent the activation of killer T cells by interacting with the APC. We show that through modulation of the activation state of an APC, such as a dendritic cell by, for example, administering antibodies which interact with the APC, the activation of a T cell is concordantly governed.

In embodiments of the present invention, we reveal novel biotechnological tools, prophylactics, therapeutics, and methods of use of the foregoing for modulating the activation state of an APC and thereby modulating the activation of a killer T cell. These embodiments have several uses and applications in the field of immunology, and enable one of skill in the art to manufacture novel pharmaceuticals, therapeutic and prophylactic agents, and vaccine components for the treatment and prevention of cancer, systemic infection, and autoimmune responses.

DETAILED DESCRIPTION OF THE INVENTION

Figure 1:
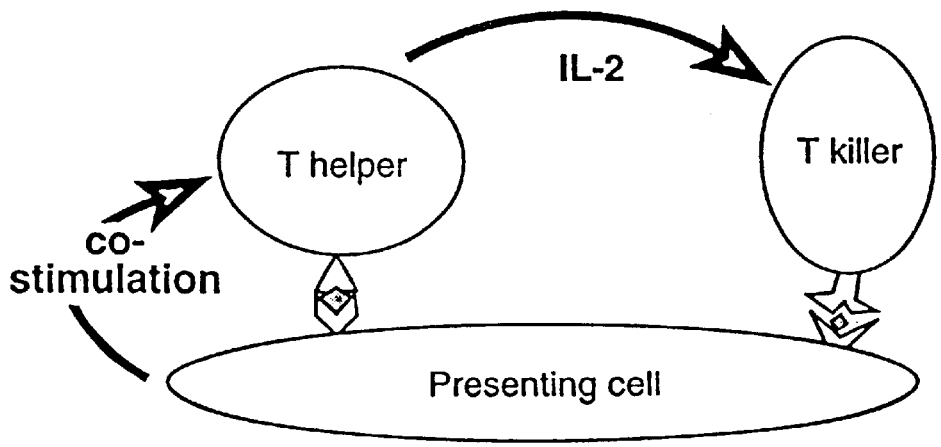
FIG. 1 illustrates two models of the delivery of help to CD8 killers. Panel A depicts the "passive" model in which the dendritic cell presents antigen to both the T helper and the killer but delivers co-stimulatory signals only to the helper, which is thereby stimulated to produce IL-2 for use by the nearby killer. Panel B depicts the "dynamic" model in which the dendritic cell offers co-stimulatory signals to both cells in that it initially stimulates the T helper, which, in turn, stimulates and "conditions" the dendritic cell to differentiate to a state where it can now directly co-stimulate the killer.
Figure 1:
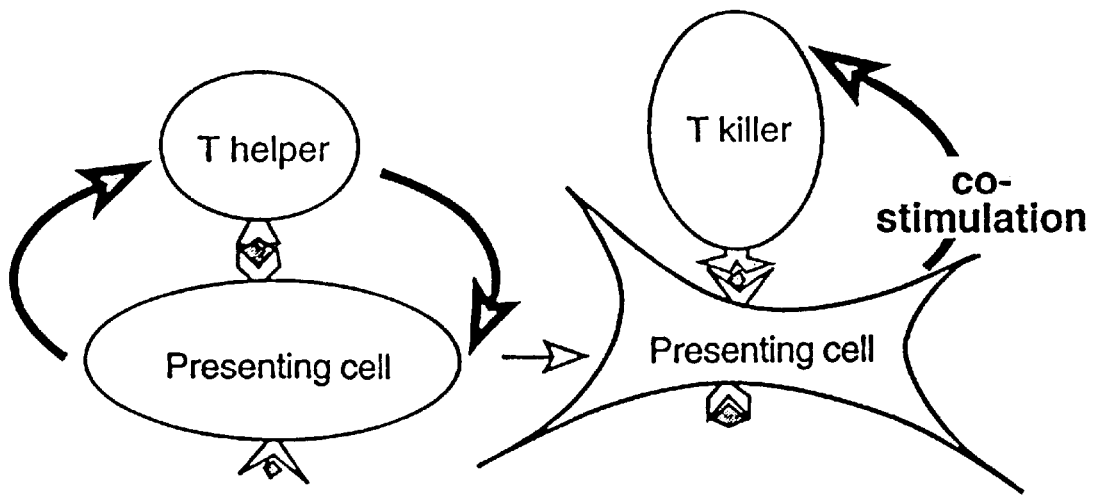

In the present invention, we demonstrate that activation of a killer T cell need not require the formation of a three-member complex having an APC, a T helper cell, and a T killer cell. (See FIG. 1, Panel A). Rather, the activation of a killer T cell can occur in a two cell complex and two sequential steps. (See FIG. 1, Panel B). Accordingly, in the first step, an APC stimulates a T helper T cell, which in turn stimulates or "superactivates" the APC to differentiate to a state where it can independently stimulate a killer T cell. In the second step, the APC encounters the killer T cell and stimulates it so that killer T cell priming is achieved in a helper independent fashion. Furthermore, we have discovered that the first step ("help") can be bypassed altogether by viral infection or an interaction with certain molecules at the cell surface of APCs. Novel biotechnological tools, prophylactics, therapeutics, diagnostics, and methods of use of the foregoing for modulating the superactivation of an APC and thereby resulting in the activation of a killer T cell are provided.

In the following disclosure several mechanisms are postulated to describe how an APC is stimulated to a state capable of killer T cell activation. These explanations are offered only to aid in the understanding of the field of the invention and consequently, they should be viewed as examples only and not limitations to embodiments of the present invention. Accordingly, the antigen specific T helper cells may stimulate the APC in a complex without a killer T cell and superactivated APCs can then prime the CD8 killer T cell. Rare, antigen-specific T helpers would then be able to make up for their scarcity by inducing the differentiation of several APCs and thereby assist many CTL precursors without the need to simultaneously contact the antigen. This model advantageously explains helper independent killer responses to certain viruses if, for example, an infected APC responds to the infection by directly undergoing superactivation.

In the discussion that follows, we disclose our discovery that help for killers can be delivered through an APC without a T helper cell/APC/killer T cell complex. Notably, we have found that $CD4^+$ T helpers can route their activity through dendritic cells (labeled by the literature as the best professional APCs). (Lassila, O. et al., Nature 318:59–62 (1985); and Steinman, R. M., Annu. Rev. Immunol. 9:271–296 (1991)). We demonstrate that activated dendritic cells cannot activate killers, although they can present antigen and stimulate $CD4^+$ T helpers to proliferate and produce cytokines. However, after an interaction with a helper T cell or antibodies to the surface molecule CD40 or viral infection, activated dendritic cells differentiate into a superactivated state in which they are able to activate killer T cells in the absence of any further need for T help.

Memory Killers are Helper Dependent

We chose to study the response to the male antigen H-Y for several reasons. First, unlike killer T cells which respond to many viruses, killer T cells which respond to H-Y have long been known to be dependent on T helper cells. (Tripp, R. A., et al., J. Immunol. 155:2955–2959 (1995); Buller, R. M. et al., Nature 328:77–79 (1987); Cardin, R. D. et al., J. Exp. Med. 184:863–871 (1996); Hou, S. et al., J. Virol. 69:1429–1434 (1995); Ahmed, R. et al. J. Virol. 62:2102–2106 (1988); Leist, T. P. et al., Scand. J. Immunol. 30:679–686 (1989); Guerder, S. & Matzinger, P., J. Exp. Med. 176:553–564 (1992); Simpson, E. & Gordon, R. D., Immunol. Rev. 35:59–75 (1977); and von Boehmer, H. et al., Proc. Natl. Acad. Sci. U.S.A. 75:2439–2442 (2978)). Second, there are few, if any, environmental antigens that cross react with H-Y. Third, T cells from normal virgin female mice do not respond to H-Y in vitro unless they have first been primed in vivo, allowing us to differentiate easily between primary and secondary responses. (Simpson, E. & Gordon, R. D., Immunol. Rev. 35:59–75 (1977) and Gray, D. & Matzinger, P., J. Exp. Med. 174:969–974 (1991)).

Figure 2:
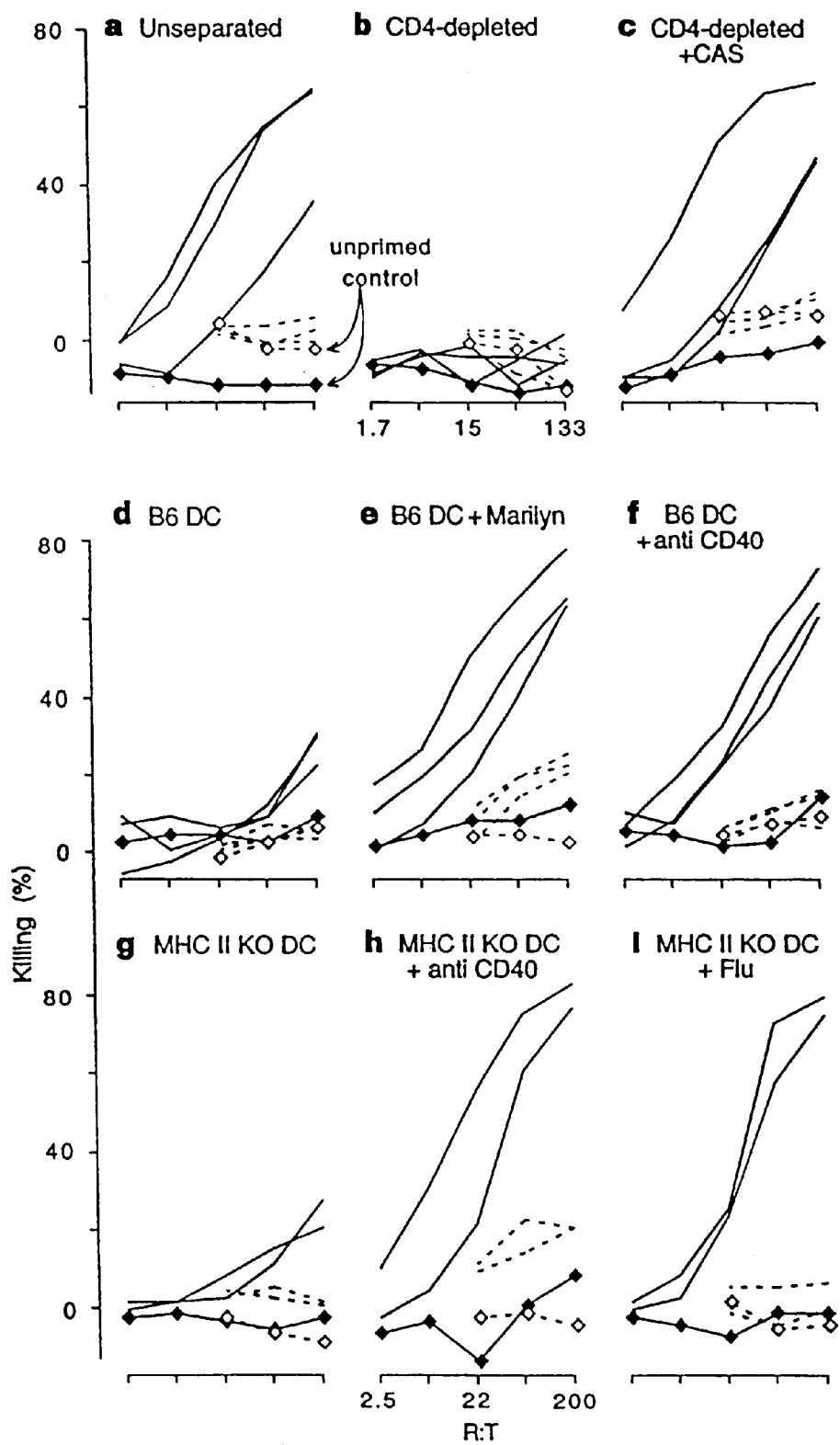
FIG. 2 shows four ways to help a killer T cell. Set 1) Unseparated (a) or CD4 depleted (b, c) spleen cells from female B6 mice were stimulated in vitro with B6 male spleen cells with or without CAS. Set 2) B6 female CD4 depleted spleen cells were stimulated in vitro with B6 male dendritic cells (dc) (d); dc+Marilyn (e); CD40 modulated dc (f); MHC class II dc (g); CD40 modulated MHC II KO dc (h); MHC II KO dc infected with Influenza (i). Solid lines indicate the killing on male targets, whereas, dashed lines indicate female targets and diamonds represent unprimed controls.

FIG. 2 illustrates the helper dependence of the CD8 T killer response and shows that T help can be delivered by soluble factors. Female C57B1/6 (B6) mice, immunized in vivo with male spleen cells, generated good in vitro killer-cell responses against male spleen stimulators (FIGS. 2a–c). The response disappeared if we depleted CD4 helpers from the responding populations just before the in vitro culture and reappeared with the addition of a supernatant from Conconavalin-A (Con-A) stimulated T cells (CAS). These data document the helper dependence of the memory anti-H-Y response and lend some support to Keene and Forman's view that help can be delivered by soluble factors. (Keene, J. A. & Forman, J., J. Exp. Med. 155:768–782 (1982)).

The following discusses our finding that an interaction with CD40 molecules of an APC activate killer T cells in the absence of T helper cells.

Help Can be Replaced through CD40

Newborn female mice, which have only a minute number of anti male T cells, and B6.bm12 mice, which carry a mutated MHC class II molecule, and are consequently deficient in H-Y specific T helpers, cannot be primed against H-Y with an injection of male spleen cells, but both types of mice respond quite well when primed with enriched, activated dendritic cells. (Matzinger, *Annu. Rev. Immunol.* 12:991–1045 (1994) and Katona et al., *J. Immunol.* 146:4215–4221 (1991)). FIGS. 2d–i show that enriched and activated dendritic cells were very inefficient at stimulating CD8 killers from which the CD4 helper cells had been completely removed, and that the response was restored by the addition of Marilyn, a CD4$^+$, H-Y specific, Th1 helper clone (FIG. 2e). Thus, a small number of helpers may go a long way, but without them, dendritic cells are unable to stimulate CD8 memory cells against H-Y.

Antibodies that were cross-linked to the surface molecule, CD40, were previously shown to stimulate B cell proliferation and enhance the function of dendritic cells to present antigen and stimulate T helper cells. (Saeland, et al., *J. Exp. Med.* 178: 113–120 (1993), Cella et al., *J. Exp. Med.* 184: 747–752 (1996), and Yang and Wilson, *Science* 273:1862–1864 (1996)). To determine whether treatment with anti-CD40 can bypass the need for T helpers in CD8 responses, we stimulated an enriched population of dendritic cells overnight by cross-linking antibodies to CD40 and found that the dendritic cells gained the ability to stimulate an anti-H-Y response (FIG. 2f).

Next, we tested whether the result with the anti-CD40 treated dendritic cells was due to the stimulation of IL-2 production from contaminating memory CD4 helper T cells. By using dendritic cells from mutant MHC class II Knock Out mice (KO), which have no MHC class II and cannot stimulate CD4 helper cells, we verified that enriched and activated KO dendritic cells, like their unmutated cousins, cannot stimulate killer responses from CD4 depleted memory populations (FIG. 2g). This result was not due to the lack of the H-Y antigen because the response is restored by the addition of an IL-2 containing supernatant. Although the absence of MHC class II molecules prevents KO dendritic cells from displaying antigen to any contaminating T helper cells, they can nevertheless be superactivated, by overnight treatment with anti-CD40 antibodies, to become excellent stimulators of a killing response (FIG. 2h). Control antibodies to dendritic cell surface antigens did not have this effect, proving that the CD40 molecule, rather than Fc receptors or other non-specific changes, were responsible.

The results above demonstrate that the requirement for help can be bypassed in two different ways: (1) by adding supernatants containing growth factors for the CD8 cells or (2) by superactivating the dendritic cells through CD40, a likely molecule to be stimulated by CD4$^+$ T helpers. After such stimulation, the superactivated dendritic cells themselves gain the ability to activate CD8 killers without the need for further interaction with a helper T cell.

In the discussion below, we show that independent antigens superactivate dendritic cells which, in turn, activate killer T cells.

Stimulation by a T Helper Independent Antigen

There are several viruses known to elicit killer responses in the absence of help. MHC class II KO or CD4 depleted mice, for example, make undiminished responses to Sendai virus, Ectromelia virus, Herpes virus and diminished but still potent responses to Lymphocytic Choriomeningitis and Influenza virus. (Tripp, R. A., et al., *J. Immunol.* 155:2955–2959 (1995); Buller, R. M. et al., *Nature* 328:77–79 (1987); Cardin, R. D. et al., *J. Exp. Med.* 184:863–871 (1996); Hou, S. et al., *J. Virol.* 69:1429–1434 (1995); Ahmed, R. et al. *J. Virol.* 62:2102–2106 (1988); and Leist, T. P. et al., *Scand. J. Immunol.* 30:679–686 (1989)). We reasoned that these viruses infect dendritic cells and induce a change in differentiation state similar to that induced by T helper cells. Evidence of this was found when we infected enriched male MHC class II KO dendritic cells with Influenza and used them to stimulate an anti-H-Y killing response from primed, CD4 depleted, B6 spleen cells. FIG. 2i shows that the infected KO dendritic cells were as potent as those stimulated with anti-CD40 in their ability to stimulate the killers.

Figure 3:
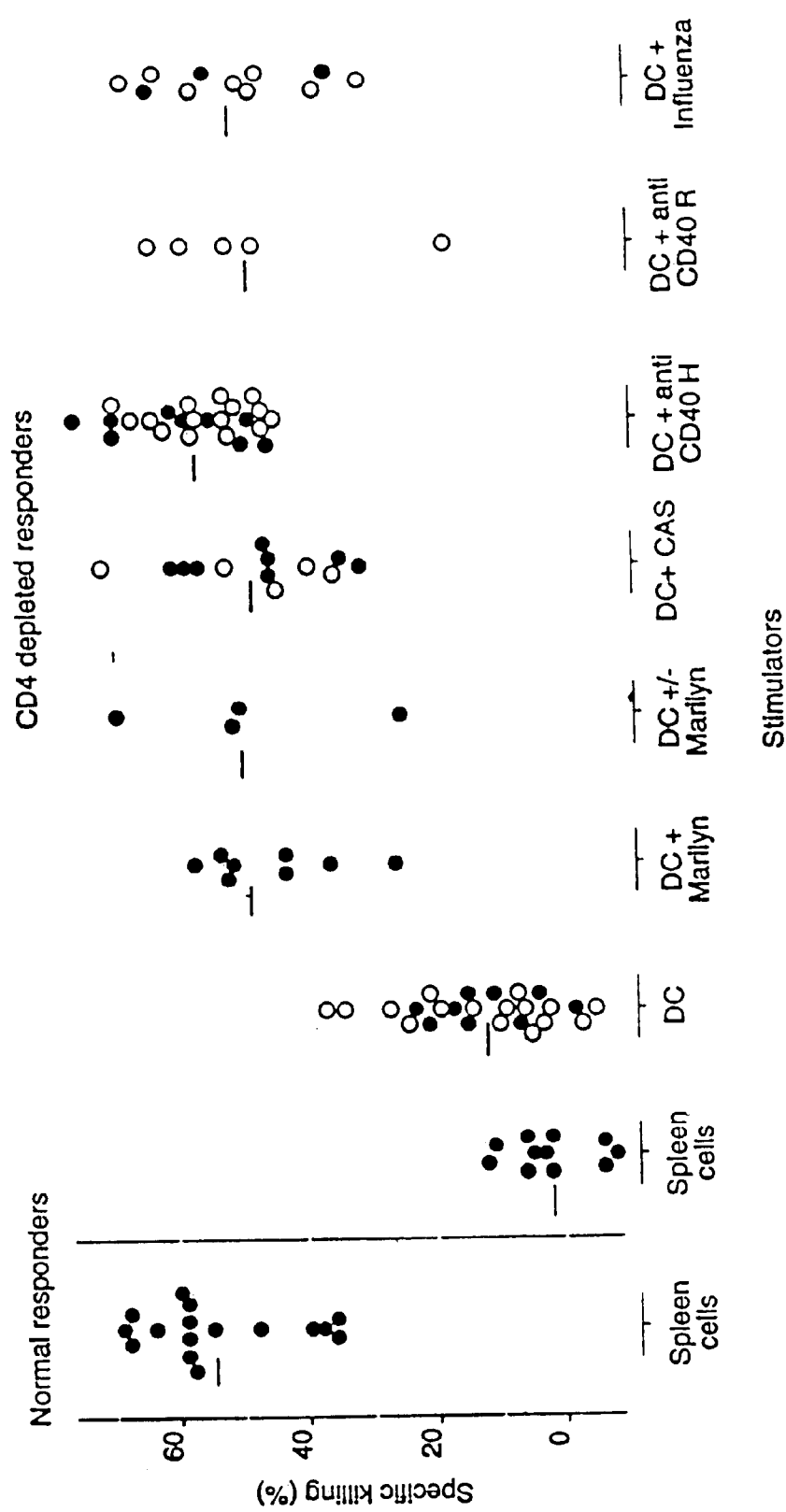
FIG. 3 shows a summary of 117 tests that demontrate five ways to help a killer T cell. Spleen cells from anti-H-Y primed female B6 mice were depleted or not of CD4 T cells and then stimulated with various normal (●) or MHC II KO (○) male stimulators. Reading left to right: spleen cells, dendritic cells (dc), dc incubated overnight with Marilyn, dc incubated overnight with Marilyn and then sorted to remove the T cells (+/− Marilyn), dc+10% CAS, dc modulated with a hamster (H) or a rat (R) anti-CD40 mAb, dc infected with influenza virus. Each point represents the killing from a single culture at an R:T ratio at which killing shown by cultures from control mice drops off plateau. Background killing on female targets is subtracted. Horizontal lines are the group average.

FIG. 3 shows a summary of the responses from 117 tests, demonstrating the range of the normal, CD4 depleted, and reconstituted responses. Although there is a certain amount of variation, it is clear that memory CD8 T killers are stimulated in vitro by normal B6 male (solid circles) and MHC class II KO male (empty circles) dendritic cells that have been superactivated by stimulation with CD4 T helpers, treatment with anti-CD40, or virus infection. The column labeled "dc+/−Marilyn" also shows that the T helper cells need not remain with the dendritic cells. Aliquots of dendritic cells that were cultured overnight with Marilyn and then FACS sorted to remove the helpers were as stimulatory as those from which the helper cells were not removed (labeled "dc+Marilyn"). Thus, a rare antigen-specific helper T cell need not communicate directly with the responding killers. It can delegate its function by superactivating a dendritic cell.

In the discussion below, we describe our discovery that agents can be administered to APCs to inhibit or prevent the superactivated dendritic cells' ability to activate killer T cells.

Blocking Surface Co-stimulatory Molecules

With B cells, unseparated spleen cells, and dendritic cells that develop from stem cells in vitro, it has been found that CD40 crosslinking leads to increased expression of several surface molecules involved in stimulation and co-stimulation of T cells, however, by FACs analysis, we did not see many of these reported changes, probably because our enriched spleen derived dendritic cells are already highly activated. (Yong, J. L. et al., *Immunity* 2:239–248 (1995); Wu, Y. & Liu, Y., *Curr. Biol.* 4:499–505 (1994); and Caux, C. et al., *J. Exp. Med.* 180:1263–1272 (1994)). We found that both the activated and the superactivated dendritic cells expressed very high and equivalent amounts of the adhesion/co-stimulatory molecules B7.1, B7.2, ICAM-1, and Heat Stable Antigen, and low levels of IL-2 receptor, FAS and FAS-ligand. Incubation with Marilyn resulted in increased expression of MHC class I and II, but neither anti-CD40 nor infection with influenza induced similar changes (though all three treatments caused minor changes in the expression of CD40 and CD1d). It did not appear, therefore, that quantitative changes in these co-stimulatory molecules account for the qualitative changes we saw in stimulatory capacity.

To determine whether the B7 molecules are involved in the stimulation of killers by superactivated dendritic cells, we included two different types of blocking reagents in the cultures; antibodies to B7.1 and B7.2, as well as a soluble form of a receptor for these two molecules, recombinant mouse CTLA-4-Ig. (Linsley et al., *Science,* 257:792–795

Figure 4:
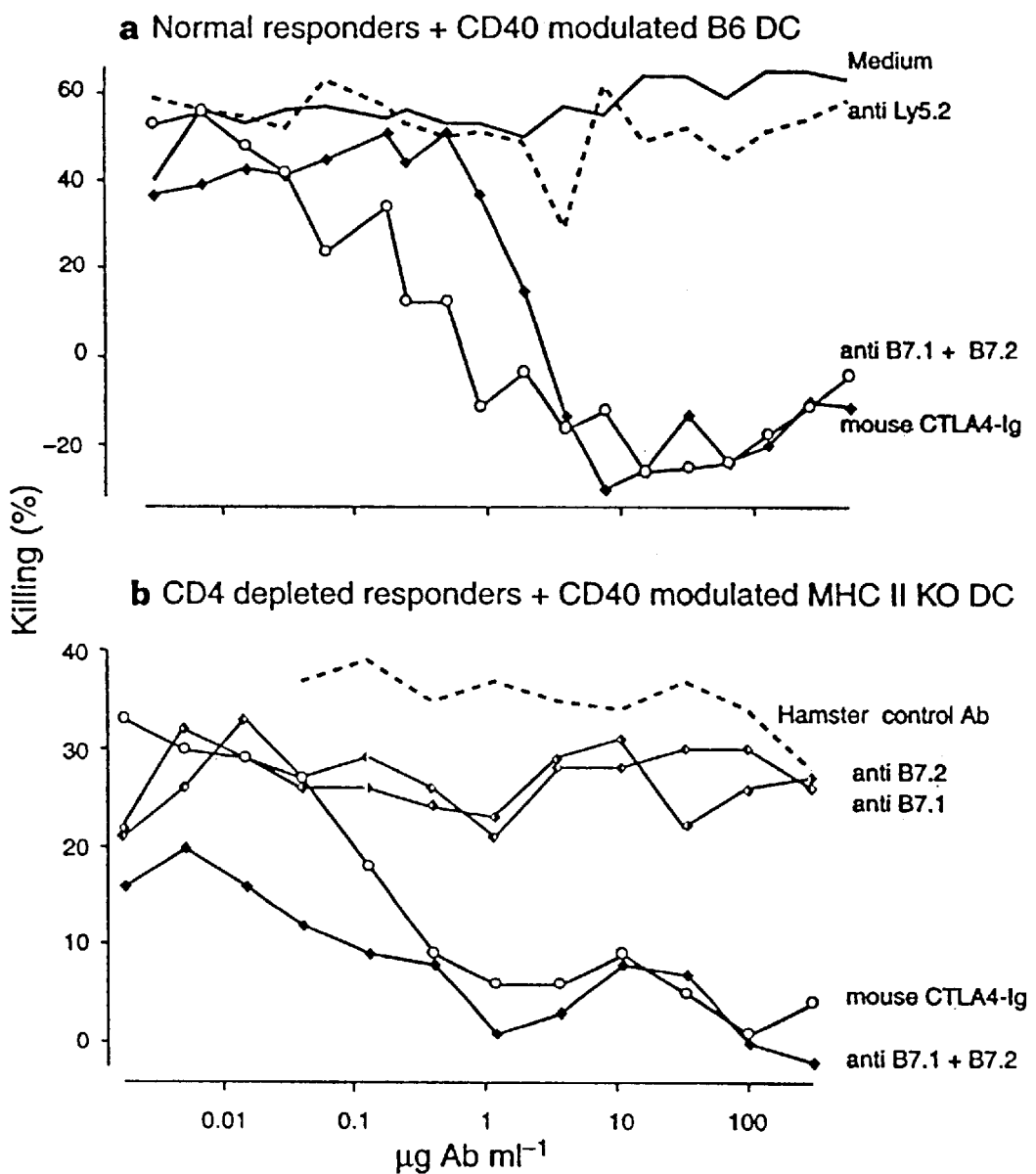
FIG. 4 shows that B7.1 and B7.2 are involved in stimulation by conditioned dendritic cells. Unseparated (expt.a) or CD4 depleted (expt. b) responders were stimulated respectively with CD40 modulated B6 or MHC II KO dc in the presence of titrated amounts of various blocking reagents.

(1992)). FIG. 4a shows that the activity of normal unseparated B6 spleen cells, responding to B6 CD40-crosslinked dendritic cells (a culture where both helpers and killers respond to the superactivated dendritic cells), was blocked by both types of reagents, and not by the non-activating control antibody, Ly5.2. In FIG. 4b, we demonstrate that the same reagents block the activity of CD4 depleted spleen cells stimulated with CD40 cross-linked MHC class II KO dendritic cells. From these results we conclude that, though the APC surface co-stimulatory molecules involved in the activation of T helper cells are not sufficient for the stimulation of killers, they are nevertheless important. Interestingly, neither anti-B7.1 nor anti-B7.2 were able to block alone, even at very high doses, while the two together blocked very well, proving that T killers are able to use the two co-stimulatory molecules interchangeably.

In addition to co-stimulatory molecules, dendritic cells can elaborate soluble factors, and CD40 stimulated dendritic cells have been shown to produce IL-12. (Cella, M. et al., *J. Exp. Med*, 184:747–752 (1996) and Koch, F. et al., *J. Exp. Med.* 184:741–746 (1996)). We therefore sought to bypass the need for help by adding IL-12 to the cultures but, unlike CAS, IL-12 did not replace the activity of helpers. The most likely scenario is that co-stimulation for a CD8, perhaps by an undiscovered co-stimulatory molecule, is similar to co-stimulation for a CD4 in that it results in the production of IL-2. (Mueller, D. L. et al., *Ann. Rev. Immunol.* 7:445–480 (1989) and Paliard, X. et al., *J. Immunol.* 141:849–855 (1988)). In support of this, we found that CD4 depleted cells produced a small amount of IL-2 when stimulated by superactivated MHC class II KO dendritic cells, whereas they produced no IL-2 when stimulated by dendritic cells cultured without a superactivating stimulus. This would explain why we can bypass the helper cell in two ways: first, by supplying the necessary IL-2 or second, by superactivating the dendritic cell to induce the CD8 killer to make its own.

We describe below several experiments in which we demonstrate that killer T cells can be stimulated in vivo.

Priming Naive T Killer Cells in vivo

There were several reasons to see whether our in vitro finding with memory killer cells could be extended to naive killers in vivo. First, naive T cells are widely thought to have more stringent activation requirements than memory T cells. (Fuchs, E. J. & Matzinger, P., *Science* 158:1156–1159 (1992); Liu, Y. et al., *J. Exp. Med.* 185:251–262 (1997); and Croft, M. et al., *J. Immunol.* 152:2675–2685 (1997)). Perhaps naive killers need a direct interaction with a helper T cell whereas memory cells do not. (Inaba, K. et al., *J. Exp. Med.* 166:182–194 (1987)). Second, in vitro and in vivo conditions do not always follow the same rules. For example, T cell populations deprived of helpers specific for sheep red blood cells are able to help for specific antibody responses in vitro but not in vivo and, conversely, cross priming for killers can occur in vivo but not in vitro. (Feeney, A. J. et al., *J. Mol. Cell Immunol.* 1:211–222 (1984) and Bevan, M. J., *J. Exp. Med.* 143:1283–1288 (1976)). Third, Mitchison's cluster model hinted that helper dependence and independence may be determined by the frequency of responders. (Michison, N. A. & O'Malley, C., *Eur. J. Immunol.* 17:1579–1583 (1987)). If the frequency is high, the response may not depend on help. Thus, as the reasoning goes, killer responses to viruses may be less dependent on help than those to H-Y simply because the frequency of responding cells is higher.

Figure 5:
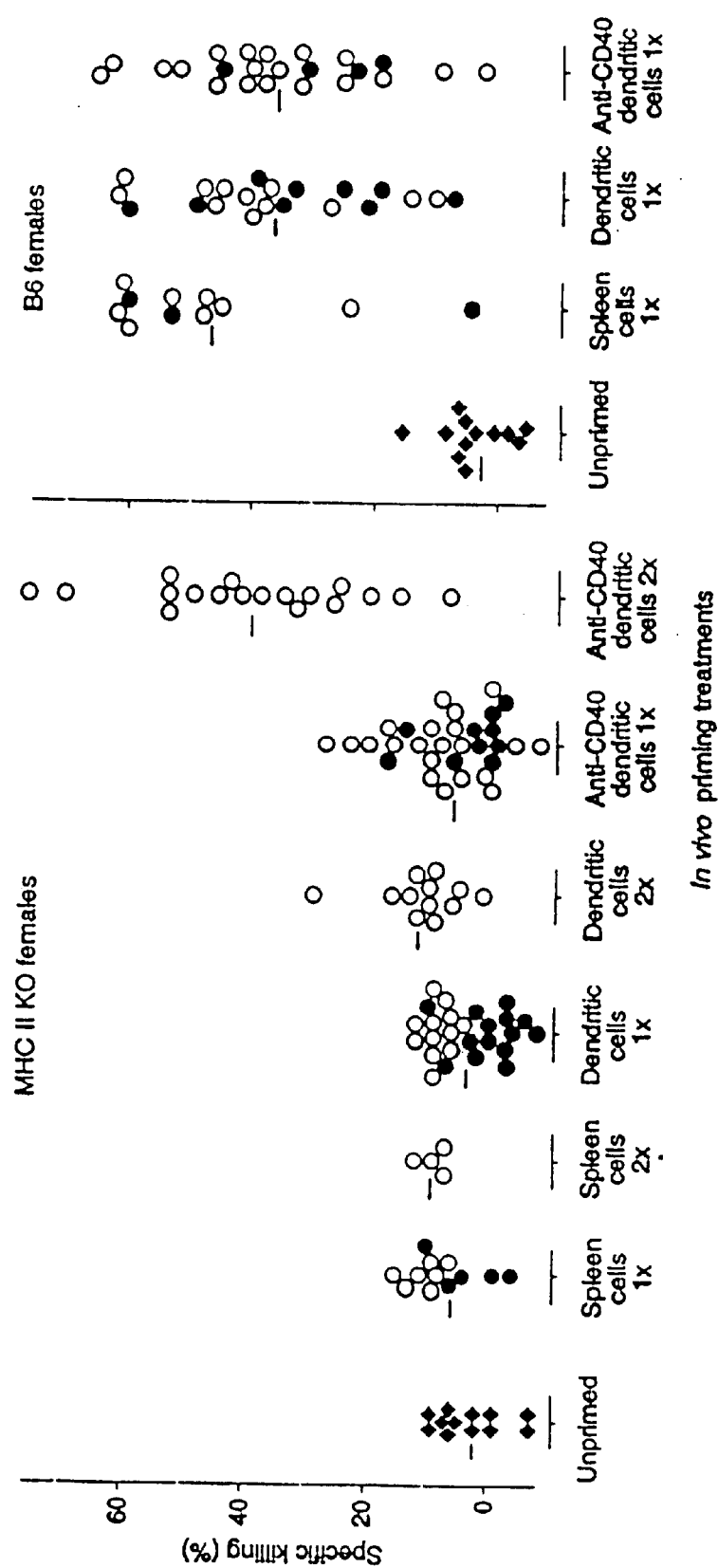
FIG. 5 shows that virgin killer T cells can be primed in vivo by CD40 modulated dendritic cells. A total of 173 B6 or MHC class II female mice were left untreated (♦) or injected once or twice with B6 (●) or MHC II KO (○) male spleen or dendritic cells that were untreated or modulated with hamster anti CD40 mAb. The in vitro cultures contained 10% CAS, which substitutes for help and allows us to concentrate on whether the mouse was primed in vivo. All mice generated CTLs to third party CBA/J targets. Representation of killing activity is as in FIG. 3.

We examined the primary anti-H-Y response of naive killers in MHC class II KO mice. As mentioned above, MHC class II KO mice are able to respond to various viruses and we found, as expected, that they would not respond to male cells. (Tripp, R. A. et al., *J. Immunol.* 155:2955–2959 (1995) and Hou, S. et al., *J. Virol.* 69:1429–1434 (1995). FIG. 5 shows that normal B6 females were primed either with male spleen or male dendritic cells whereas the KO mice were unresponsive to both. Because of the possibility that the lack of response was due to a lack of help in the in vitro culture, rather than a lack of help during priming in vivo, we also tested these cells in cultures to which we added an exogenous source of helper factors. In neither case did the killers from the KO mice respond to male stimulators. Thus, though activated male dendritic cells can prime virgin bm12 mice (where help is limited), they cannot, by themselves, prime anti-H-Y killers in the MHC class II KO mice, where help is absent. (Boog, C. J., *Nature* 318:59–62 (1985)).

Next, we tested whether stimulation with anti-CD40 turns a dendritic cell into a superactivated APC that is able to prime naive T killer cells. Surprisingly, it does. FIG. 5 is a summary of 173 female MHC class II KO or B6 mice that were primed in vivo with male spleen cells, cultured activated dendritic cells, or anti-CD40 treated superactivated dendritic cells, and then restimulated in vitro in the presence of supernatants containing soluble helper factors. By replacing the need for help in the in vitro culture, we were able to concentrate on the in vivo priming step, since only primed killers can respond in vitro. We found that the KO mice were able to respond well only if they had been primed with anti-CD40 treated dendritic cells, and then only if they were immunized twice. Thus, the helper requirement for virgin T killer cells, like that for memory T killer cells, can be bypassed by superactivated APCs.

The requirement for repeated immunization is intriguing. It may be that superactivated dendritic cells do not home as efficiently to lymph nodes as untreated cells, perhaps because of antibody remaining on their surface, or perhaps because they have differentiated to a state in which, under normal circumstances, they would have already migrated to the lymph node and would not be required to wander further. Alternatively, the reason may have to do with time rather than geography. An encounter between killer and dendritic cells may take a couple of days in vivo whereas it only takes a couple of hours in vitro. If the superactivated state is not eternally stable, many of the injected dendritic cells may have reverted (or died) before they can be seen by a killer. The superactivated state may last a couple of days. In many experiments, we saw that normally cultured dendritic cells were able to stimulate weakly. We surmise that this may be due to the presence of a small percentage of dendritic cells that had been superactivated in vivo by T helper cells responding to environmental antigens and that maintained their stimulatory ability during the two day preparatory cultures.

There are several systems in which two cells communicate through a third. In every case but that of the T helper with its corresponding T killer, the interactions are either mediated by soluble factors that traverse the distances required (such as the regulatory feedback mechanisms in the hypothalamo-pituitary-adrenal axis) or are facilitated by stable geometries in which the cells involved remain linked for their entire lives (as in the nervous system). Neither of these mechanisms works for cells of the immune system, where the communicating cells are rare and migratory. The two-cell interactions between antigen specific T helpers and their corresponding B cells are facilitated by structures in lymph nodes, to which local tissue fluids drain and where the two circulating cells can find each other during an infection.

(Anderson, A. O. & Shaw, S., *Semin. Immunol.* 5:271–282 (1993)). However, faced with an almost impossible interaction of three migratory cells, two of which are rare (the T helper and killer) and one of which is both rare and transient (the antigen loaded APC), the immune system adds the fourth dimension, time, and transforms the three cell interaction into a series of consecutive two cell engagements. The first, between a T helper and an activated antigen presenting cell, induces the APC to differentiate to a superactivated state in which it can engage in the second, and stimulate a T killer cell.

Mediating the help function through superactivated APCs solves more than just the rarity problem. Helpers need not excessively secrete IL-2 into their surroundings. Killers do not need to wait for a co-stimulatory signal or help after binding to antigen, since both the antigen and the co-stimulatory signals come from APCs and can be delivered simultaneously, as they are to helpers. Furthermore, the activity of a few helpers is amplified, since a single T helper cell can "arm" a number of APCs which can then, in their turn, activate a multitude of killers.

Superactivation of APCs also provides an explanation for the contradictions about the helper independence of CTL. Dendritic cells, like many other cells, react directly to a virus infection. Whereas keratinocytes, for example, respond to virus by producing interferon, dendritic cells respond by becoming superactivated and able to activate killer T cells. (Torseth, J. W. et al., *J. Infect. Dis.* 155:641–648 (1987)). Our discovery explains the helper independent responses to virus in the class II KO mice. It also explains why some anti-viral responses depend more heavily than others on T helpers. For example, the KO mice respond as well as wild type mice to Sendai virus but less well than wild type mice to Influenza virus. For these viruses, we believe that two types of dendritic cells present viral antigens to CD8 killers. There are those that are infected and consequently superactivated and are able to activate killers in the absence of help. However, there are others that have become activated by danger signals at the site of infection but which are not themselves infected. (Matzinger, P., *Annu. Rev. Immunol.* 12:991–1045 (1994)). Though they will have picked up the viral antigens from dead and dying infected cells in their surroundings, they cannot become superactivated in the absence of help and, thus, in a KO mouse, will be unable to stimulate CD8 killers. A corollary is that the helper independence of a CD8 response to a particular virus correlates directly with the virus's ability to infect and superactivate APCs.

As seen in FIGS. 2i and 3, superactivation by viruses also substitutes for help in responses directed at non-viral antigens that are presented by the same APC. This finding explains why the subject of help for killers has been fraught with contradictions. For example, in an earlier study with responses to Qa-1, we found that the killer responses were independent of help during a mouse hepatitis virus infection in the animal colony. (Guerder, S. & Matzinger, P., *J. Exp. Med.* 186:553–564 (1992)). In the current study, for a period of about four months, a low but nevertheless substantial response to H-Y remained in CD4 depleted CD8 memory cells. This helper "independent" aspect of the response disappeared when we purchased mice from another source colony (though no known pathogen was found in the first colony). Thus, depending on the health status of a mouse colony, various responses appear to be dependent on or independent of T help. (Keene, J. A. & Forman, J., *J. Exp. Med.* 155:768–782 (1982); Guerder, S. & Matzinger, P., *J. Exp. Med.* 186:553–564 (1992); Guerder, S. & Matzinger, P.,

*Cold Spring Harb. Symp. Quant. Biol.* 54:799 (1989); Rees, M. A. et al., *Proc. Natl. Acad. Sci. U.S.A.* 87:2765–2769 (1990); Simpson, E. & Gordon, R. D., *Immunol. Rev.* 35:59–75 (1977); von Boehmer, H. et al., *Proc. Nat. Acad. Sci. U.S.A.* 75:2439–2442 (1978); Fuchs, E. J. & Matzinger, P., *Science* 258:1156–1159 (1992); Auchincloss, H., Jr. et al. *Proc. Natl. Acad. Sci. U.S.A.* 90:3373–3377 (1993); Boog, C. J. et al., *Nature* 318:59–62 (1985); Shimuzu, T. & Takeda, S., *Eur. J Immunol.* 27:500–508 (1997); Roopenian, D. C. et al., *J. Immunol.* 130:542–545 (1983); and Rosenberg, A. S. et al., *Nature* 322:829–831 (1986)).

Finally, the existence of superactivated dendritic cells makes it clear that there are several activation states for dendritic cells, in analogy to the multiplicity of activation states seen with other cells of the immune system. In the case of B cells, for example, signals from T helper cells do more than simply evoke activation signals. They also persuade B cells to switch to the production of different classes of antibody. Thus, Th1 helper T cells induce the production of the complement fixing antibody, IgG2a, whereas Th2 helpers elicit IgE and IgG1, and Th3 helpers signal the production of IgA. (Katona et al., *J. Immunol.* 146:4215–4221 (1991), Chen et al., *Science* 265:1237–1240 (1994), and Stavnezer, J. *Immunol.* 155:1647–1651 (1995)). Similarly, dendritic cells are influenced by the signals they receive to differentiate to different states of superactivation, each one involved in a different class of response. We have shown here that dendritic cells cultured with Th1 helpers or virus become adept at activating CD8 killers. There is also some evidence that the presence of IL-10 or fluid from the anterior chamber of the eye can prompt APCs to become good inducers of TH2 rather than Th1 responses. (Liu, L. et al., *Adv. Exp. Med. Biol.* 417:375–381 (1997) and Wilbanks, G. A. & Streilien, J. W., *Eur. J Immunol.* 22:1031–1036 (1992)). The dendritic cell is a cell type which responds to its environment in several ways and, in turn, influences several aspects of an immune response. First, it is activated by exogenous or endogenous danger signals to capture, process, and present antigen along with co-stimulatory signals and thus initiate an immune response. (Janeway, C. A., Jr., *Cold Spring Harb. Symp. Quant. Biol.* 54 Pt 1:1–13 (1989) and Matzinger, P., *Annu Rev. Immunol.* 12:991–1045 (1994)). Further, it is also influenced by the cells, cytokines, and other signals in its environment to modify the response that it initiates, so that the response is appropriate for both the pathogen it is directed against and the location in which it unfolds.

In the discussion below, we describe several methods of molecular modeling and rational drug design for the identification of more ligands which superactivate an APC or block, inhibit, or prevent the activation of killer T cells.

Methods of Rational Drug Design

Combinatorial chemistry is the science of synthesizing and testing compounds for bioactivity en masse, instead of one by one, the aim being to discover drugs and materials more quickly and inexpensively than was formerly possible. In some embodiments, search programs are employed to compare regions of ligands which superactivate an APC or inhibit the superactivation of killer T cells with other molecules, such as peptides, peptidomimetics, and chemicals, so that therapeutic interactions of the molecules can be predicted and new derivative ligands can be designed. (Schneider, *Genetic Engineering News* December: page 20 (1998), Tempczyk et al., *Molecular Simulations Inc. Solutions* April (1997), and Butenhof, *Molecular Simulations Inc. Case Notes* (August 1998)). This process of directed combinatorial chemistry is referred to as "rational drug design". One goal of rational drug design is to produce structural analogs of biologically active polypeptides of interest or of small molecules with which they interact (e.g., agonists, antagonists, null compounds) in order to fashion drugs which are, for example, more or less potent forms of the ligand. (See, e.g., Hodgson, *Bio. Technology* 9:19–21 (1991)). Rational drug design has been used to develop HIV protease inhibitors and agonists for five different somatostatin receptor subtypes. (Erickson et al., *Science* 249:527–533 (1990) and Berk et al., *Science* 282:737 (1998)).

In one approach, a three-dimensional structure of a ligand of interest (e.g., a polypeptide or fragment corresponding to a ligand which interacts with CD40 or a ligand for CD40) is determined by x-ray crystallography, NMR, or neutron diffraction and computer modeling. Useful protein models of the ligand are also gained by computer modeling alone. Combinatorial chemistry is then employed to design derivatives of the ligand of interest based on the three-dimensional models. The APC superactivation, killer T cell activation, and superactivation blocking assays, described above and in Ridge et al., *Nature* 393:474 (1998) (referred to collectively as "superactivation assays") are performed on the derivative ligands and classes of ligands based on the potency of APC superactivation and killer T cell activation are recorded on a computer readable media. Further cycles of modeling and superactivation assays are employed to more narrowly define the parameters needed in a ligand which elicits a desired response.

For example, chemical libraries and databases are first searched for molecules similar in structure to one or more ligands which interact with the APC at a specific site and produce a desired APC response (e.g., anti-CD40 antibodies—FGK45, HM40-3, 3/23, 5C3, Mab-89, BE-1, EA5, and M3 or other antibodies—anti-B7.1(17A10), anti-B7.2 (2D10), CTLA-4-Ig, and MR1 and antibodies which recognize a CD40 ligand). Identified candidate ligands are then screened in the superactivation assays, described above, and the compounds which produce the desired superactivation state are used as templates for further library construction. Libraries of derivative ligands are synthesized on solid support beads by split-and-pool synthesis, a multistage process for producing very large numbers of compounds. The support-bound compounds are then used in superactivation assays or "free mixtures" are created by cleaving the compound from the support and these free mixtures are screened in the superactivation assays. Compounds which produce desirable APC responses are identified, recorded on a computer readable media, and the process is repeated to select for optimal ligands.

Each compound and its response in a superactivation assay is recorded on a computer readable media and a database or library of compounds and respective APC responses is generated. These databases or libraries are used by researchers to identify important property differences between active and inactive molecules so that compound libraries are enriched for ligands which have favorable characteristics. Further, enrichment can be achieved by using approaches in dynamic combinatorial chemistry. (See e.g., Angnew, *Chem. Int. Ed.*, 37:2828 (1998)). For example, an APC target biomolecule, such as CD40, is joined to a support and is bound by the compounds from the libraries generated above. The CD40 resin bound with one or more candidate ligands is removed from the binding reaction, the ligands are eluted from the support, and are identified. Cycles of immobilized target binding assays are conducted, classes of ligands which exhibit desired binding characteristics are identified, and this data is recorded on a computer readable media and is used to select more ligands which produce a desired APC response.

In addition, a ligand peptide of interest (e.g., anti-CD40 antibodies—FGK45, HM40-3, 3/23, 5C3, Mab-89, BE-1, EA5, and M3 or other antibodies—anti-B7.1(17A10), anti-B7.2 (2D10), CTLA-4-Ig, and MR1 and antibodies which recognize CD40 ligands) is analyzed by an alanine scan (Wells, *Methods in Enzymol.* 202:390–411 (1991)). In this technique, an amino acid residue is replaced by alanine, and its affect on the peptide's activity is measured by a functional assay, such as the superactivation assays described herein. Each of the amino acid residues of the peptide is analyzed in this manner and the important regions of the peptide are identified. Subsequently, this functionally important region is recorded on a computer readable medium, stored in a first database in a computer system, and a search program is employed to generate a protein model of the functionally important region. Once a protein model of the functionally important region has been generated, a second database comprising one or more libraries having peptides, chemicals, peptidomimetics and other agents is accessed by a search program and individual agents are compared to the protein model to identify agents which comprise homologous regions or domains which resemble the identified functionally important region. Agents identified by the approach above are then tested in the superactivation assays and are used to construct multimeric agents and/or are incorporated into pharmaceuticals, as detailed below.

In another embodiment, computer modeling and the sequence-to-structure-to-function paradigm is exploited to identify superactivating ligands or ligands which inhibit the superactivation of killer T cells. By this approach, first the structure of a protein ligand having a known response in a superactivation assay is determined from its sequence using a threading algorithm, which aligns the sequence to the best matching structure in a structural database. Next, the protein's active site (i.e., the site important for a desired response in the superactivation assay) is identified and a "fuzzy functional form" (FFF)—a three-dimensional descriptor of the active site of a protein—is created. (See e.g., Fetrow et al., *J. Mol. Biol.* 282:703–711 (1998) and Fetrow and Skolnick, *J. Mol. Biol.* 281: 949–968 (1998)).

The FFFs are built by itteratively superimposing the protein geometries from a series of functionally related proteins with known structures. The FFFs are not overly specific, however, and the degree to which the descriptors is relaxed is explored. In essence, conserved and functionally important residues for a desired T cell response are identified and a set of geometric and conformational constraints for a specific function are defined in the form of a computer algorithm. The program then searches experimentally determined protein structures from a protein structural database for sets of residues that satisfy the specified constraints.

By using this computational protocol, genome sequence data bases such as maintained by various organizations are screened for specific protein active sites and for identification of the residues at those active sites which resemble a desired ligand. Databases of short sequence patterns or motifs designed to identify a given function or activity are also screened. Several other groups have developed such databases. These databases, notably Prosite, Blocks, and Prints, use short stretches of sequence information to identify sequence patterns that are specific for a given function; thus they avoid the problems arising from the necessity of matching entire sequences. By these approaches, new ligands are rationally selected for further identification by the superactivation assay methods, described above. Rounds or cycles of superactivation assays on the molecules and derivatives thereof and further FEE refinement and database searching allows us to more narrowly define classes of ligands which produce desirable killer T cell responses.

Many computer programs and databases are used with embodiments of the invention to identify agents which modulate superactivation of an APC. The following list is intended not to limit the invention but to provide guidance to programs and databases which are useful with the approaches discussed above. The programs and databases include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990)), FASTA (Pearson and Lipman, *Proc. Natl. Acad. Sci. USA*, 85: 2444 (1988)), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), Modeller 4 (Sali and Blundell J. Mol. Biol. 234:217–241 (1997)), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, and the BioByteMasterFile database. Many other programs and data bases would be apparent to one of skill in the art given the present disclosure.

In the discussion that follows, several superactivation assays are described for the determination of a ligand's capacity to superactivate an APC or block, inhibit, or prevent superactivation of an APC and thereby modulate killer T cell activation.

Identification of Ligands Which Modulate Superactivation of an APC

In the experiments presented above, we demonstrated that antibodies to CD40 and influenza virus superactivate an APC, a dendritic cell, and that antibodies to the B7.1 and B7.2 molecules block the ability of APCs to activate a killer T cell. The term "superactivation" refers to an APC activation state which allows for the activation of killer T cells at a level above that exhibited by an unstimulated APC. The activation state of an APC can be expressed in terms of the percentage killing of a pathogen, for example. That is, the capacity of killer T cells to kill a pathogen having an antigen in the absence of helper T cells which is presented by an APC is directly related to the activation state of an APC. A simply "active" APC exhibits a percentage killing on the order of 0–10%, whereas, a "superactivated" APC desirably exhibits a percentage killing between 20% and 100% and preferably between 30% and 100%. A superactivated APC, for example, exhibits a percentage killing of at least 20% or 22% or 24% or 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or about 100%. Superactivation and the activation state of an APC can be measured by more direct biochemical approaches as will be apparent to one of skill in the art given this disclolsure.

Candidate ligands, ligands selected by the rational drug design approaches discussed above, for example, and randomly selected ligands are, desirably, screened by several "superactivation assays" so as to determine the candidates ability to superactivate an APC or inhibit T cell activation. One type of superactivation assay, as described above, contacts an APC, such as a dendritic cell, with a ligand in the absence of T helper cells and the ligand-stimulated APC is then contacted with killer T cells. Subsequently, the killer T cells are analyzed for their ability to kill a pathogen having the antigen presented by the APC and the percentage of killing—a measure of the activation state of the APC—is recorded on a computer readable media. Other ways of measuring the activation state of an APC or a killer T cell, such as by biochemical approaches, are within the scope of embodiments of the present invention and are encompassed with the meaning of the term "superactivation assay."

Libraries of information on ligands and their corresponding superactivation state measurements for specific APCs and pathogens and/or specific antigens are generated by performing the superactivation assays described above and a record of the results is generated and stored on a computer readable media. Databases of this information is valuable to investigators and clinicians for selecting the type of ligand-based pharmaceutical to treat a particular disease. Preferable libraries are created by performing the superactivation assays above on the ligands FGK45, HM40-3, 3/23, 5C3, Mab-89, BE-1, EA5, M3 17A10, 2D10, CTLA-4-Ig, and MR1 and antibodies which recognize CD40 ligands and fragments or derivatives therof. These libraries are also used to map the active regions of the ligands and new ligands which produce a desired killer T cell response are identified using this information and the methods presented above.

The immune responsiveness of a subject to a ligand is also predicted using the assays detailed above. Accordingly, an APC provided from a subject is contacted with a ligand in the absence of T helper cells and the activation state of the APC is determined. The immune responsiveness of the subject is then measured by determining the relative level of activation of the APC, wherein an activation state exhibiting a killing percenatge of 20% to 100% indicates a good immune responsiveness and an activation state exhibiting a killing percentage of 0% up to 20% indicates a poor immune responsiveness. A good immune responsiveness, for example, is indicated by superactivated APCs which exhibit a killing percentage of at least 20% or 22% or 24% or 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or about 100%. In preferable embodiments, the ligand is selected from FGK45, HM40-3, 5C3, Mab-89, BE-1, EA5, M3, 3/23, 17A10, 2D10, CTLA-4-Ig, and MR1 and antibodies which recognize CD40 ligands and fragments or derivatives therof. A preferable APC is a dendritic cell. By using this approach to determine the immune responsiveness of a subject to a particular antigen present in a cancer cell or pathogen, for example, ligands which provide the best APC and killer T cell response for the particular antigen are identified and these ligands are selected for incorporation into pharmaceuticals.

A kit to identify immune responsiveness is another embodiment. One such kit comprises an APC (preferably a dendritic cell), a ligand that is recognizable by the APC (preferably one or more of the antibodies or fragments or derivatives of FGK45, HM40-3, 3/23, 17A10, 5C3, Mab-89, BE-1, EA5, M3, 2D10, CTLA-4-Ig, and MR1 and antibodies which recognize CD40 ligands), a means for contacting the APC with the ligand, a means to analyze the activation state of the APC, and a means to measure the immune responsiveness, wherein superactivation indicates a good immune responsiveness and an activation state below superactivation indicates a poor immune responsiveness. Several means for contacting the APC with a ligand are used with this embodiment and the bound-support agents and the pharmaceutical preparations, described below, are examples. The activation state of the APC is frequently measured indirectly by monitoring the percentage killing by killer T cells, as described previously, or by biochemical assays as known to those of skill in the art. The means to measure immune responsiveness often times depends on the means used to measure the activation state of the APC but generally includes the detection of markers such as radioactivity, fluorescence, magnetism, including automated detection approaches as known in the art.

In the dislcosure below, we teach the preparation of multimeric supports having ligands which modulate APC superactivation and thereby modulate killer T cell activity. These multimeric supports have many uses including, but not limited to, the manufacture of biotechnological tools and components for pharmaceuticals, therapeutic and prophylactic agents.

Preparation of Multimeric Supports and Multimerized Ligands

A useful biotechnological tool or a component to a prophylactic or therapeutic agent provides a ligand in such a form or in such a way that a sufficient affinity or superactivation of the APC or inhibition/prevention of superactivation of the APC is obtained. While a natural monomeric ligand (i.e. appearing as a discrete unit carrying only one binding epitope) is sufficient to superactivate an APC or inhibit superactivation of an APC, a synthetic ligand or a multimeric ligand (i.e. appearing as a multiple unit of the compound having several binding epitopes) often times has greater ability to superactivate an APC or inhibit superactivation of an APC. It should be noted that the term "multimeric" refers to the presence of more than one unit of a ligand, for example, several individual molecules of an antibody, as distinguished from the term "multimerized" which refers to the presence of more than one ligand joined as a single discrete unit, for example several antibody molecules joined in tandem.

A multimeric agent (synthetic or natural) which modulates the superactivation of an APC is obtained by coupling a ligand to a macromolecular support. A "support" is also termed a carrier, a resin or any macromolecular structure used to attach or immobilize a ligand. Solid supports include, but are not limited to, the walls of wells of a reaction tray, test tubes, polystyrene beads, magnetic beads, nitrocellulose strips, membranes, microparticles such as latex particles, sheep (or other animal) red blood cells, Duracyte® artificial cells, and others. In several emodiments, the macromolecular support has a hydrophobic surface which interacts with a portion of the ligand by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, the ligand is covalently bound to carriers including proteins and oligo/polysaccharides (e.g. cellulose, starch, glycogen, chitosane or aminated sepharose). In these later embodiments, a reactive group on ligand, such as a hydroxy or an amino group, is used to join to a reactive group on the carrier so as to create the covalent bond. Embodiments also comprise a support with a charged surface which interacts with the ligand. Additional embodiments comprise a support which has other reactive groups that are chemically activated so as to attach a ligand, such as a peptide or chemical compound. For example, cyanogen bromide activated matrices, epoxy activated matrices, thio and thiopropyl gels, nitrophenyl chloroformate and N-hydroxy succinimide chlorformate linkages, or oxirane acrylic supports are used. (Sigma).

Inorganic carriers, such as silicon oxide material (e.g. silica gel, zeolite, diatomaceous earth or aminated glass) to which the ligand is covalently linked through a hydroxy, carboxy or amino group and a reactive group on the carrier are also embodiments. Furthermore, in some aspects, a liposome or lipid bilayer (natural or synthetic) is used as a support and ligands are attached to the membrane surface or are incorporated into the membrane by techniques in liposome engineering. By one approach, liposome multimeric supports comprise fusion proteins having a first domain which interacts with a molecule on the surface of an APC and a second domain which anchors the protein to the lipid bilayer. The anchor is constructed of hydrophobic amino acid residues, resembling known transmembrane domains, or comprises ceramides that are attached to the first domain by conventional techniques.

Carriers for use in the body, (i.e. for prophylactic or therapeutic applications) are desirably physiological, non-toxic and preferably, non-immunoresponsive. Contemplated carriers for use in the body include poly-L-lysine, poly-D, L-alanine and Chromosorb® (Johns-Manville Products, Denver Colo.). Ligand-conjugated Chromosorb® (Synsorb-Pk) has been tested in humans for the prevention of hemolyticuremic syndrome and was reported as not presenting adverse reactions. (Armstrong et al. *J. Infectious Diseases* 171:1042–1045 (1995)). For some embodiments, the administration of a "naked" carrier (i.e., lacking an attached ligand) which has the capacity to attach a ligand which modulates APC superactivation and killer T cell activation inside the body of a subject is performed. By this approach, a "prodrug-type" therapy is administered in which the naked carrier is provided separately from the desired ligand and, once both are in the body, the carrier and the ligand assemble into a multimeric complex and superactivate an APC.

In another embodiment, linkers, such as λ linkers, of an appropriate length are inserted between the ligand and the support so as to encourage greater flexibility in the ligand and thereby overcome any steric hindrance which is presented by the support. The determination of an appropriate length of linker which allows for optimal binding and superactivation of the APC or inhibition of superactivation of the APC, is made by screening the ligands with varying linkers in the superactivation assays detailed in the present disclosure.

A composite support comprising more than one type of ligand is also an embodiment. A "composite support" is a carrier, a resin, or any macromolecular structure used to attach or immobilize two or more different ligands which modulate the superactivation of an APC. In some embodiments, a liposome or lipid bilayer (natural or synthetic) is used in constructing a composite support and ligands are attached to the membrane surface or are incorporated into the membrane using techniques in liposome engineering. By one approach, a liposome composite support comprises fusion proteins having a first domain which interacts with a molecule on the surface of an APC and a second domain which anchors the protein to the lipid bilayer. The anchor is constructed of hydrophobic amino acid residues, resembling known transmembrane domains, or comprises ceramides that are attached to the first domain by conventional techniques Many different fusion proteins are created in this manner and are incorporated into a liposome so as to create the various aspects of composite supports of the present invention. The composite supports are also constructed by utilizing hydrophobic interactions and covalent linkages formed through reactive groups, as detailed above.

Linkers, such as λ linkers, of an appropriate length between the ligands and the support are inserted in some embodiments so as to encourage greater flexibility in the molecule and overcome steric hindrance. The determination of an appropriate length of linker which allows for optimal binding and superactivation of the APC or inhibition of superactivation of the APC, is made by screening the ligands with varying linkers in the superactivation assays detailed in the present disclosure.

In other embodiments of the present invention, the multimeric and composite supports discussed above have attached multimerized ligands so as to create a "multimerized-multimeric support" and a "multimerized-composite support", respectively. An embodiment of a multimerized ligand, for example, is obtained by coupling two or more nucleotide sequences encoding the ligand protein or fragments thereof in tandem using conventional techniques in molecular biology. The multimerized form of the ligand is advantageous for many applications because of the ability to obtain an agent with a better ability to superactivate an APC or prevent the superactivation of an APC. The incorporation of linkers or spacers, such as flexible λ linkers, between the protein domains which make-up the multimerized agent is also advantageous for some embodiments. The insertion of λ linkers of an appropriate length between protein binding domains, for example, encourages greater flexibility in the molecule and overcomes steric hindrance between the several proteins. Similarly, the insertion of linkers between the multimerized ligand and the support encourages greater flexibility and reduces steric hindrance presented by the support. The determination of an appropriate length of linker which allows for optimal binding and superactivation of the APC or inhibition of superactivation of the APC, is made by screening the ligands with varying linkers in the superactivation assays detailed in this disclosure.

In desirable embodiments, the various types of supports discussed above are created using proteins or fragments thereof which interact directly or indirectly with a CD40 molecule of an APC. In preferred embodiments, for example, the multimeric supports, composite supports, multimerized-multimeric supports, or multimerized-composite supports, collectively referred to as "support-bound agents", have proteins which comprise domains found in anti-CD40 antibodies such as FGK45, HM40-3, 3/23 5C3, Mab-89, BE-1, EA5, and M3. Additional embodiments include support-bound agents having proteins which comprise domains found in the anti-B7.1 (17A10), anti-B7.2 (2D10), CTLA-4-Ig antibodies, MR1 antibodies and antibodies which recognize CD40 ligands. In one embodiment, a composite support comprises both anti-B7.1 (17A10) and anti-B7.2 (2D10) antibodies so as to create a support-bound agent which effectively blocks APC superactivation and, concomitantly, activation of killer T cells.

In the discussion below, we describe several embodiments of the present invention which have therapeutic and/or prophylactic application.

Therapeutic and Prophylactic Embodiments

In the therapeutic and prophylactic embodiments of the present invention, the ligands identified as superactivating an APC or blocking, inhibiting, or preventing the activation of a killer T cell (collectively referred to as "superactivation modulating agents") are incorporated into a pharmaceutical product and are administered to a subject in need. One contemplated method of making a pharmaceutical involves the selection of a ligand which directly or indirectly interacts with CD40 of an APC and thereby superactivates the APC. Preferably, a protein, polypeptide fragment, or peptidomimetic, including but not limited to, FGK45, HM40-3,3/23, 5C3, Mab-89, BE-1, EA5, and M3 or fragments or derivatives thereof is selected and is incorporated into a pharmaceutical by conventional techniques. Desirably, the ligand which is incorporated into the pharmaceutical interacts with a CD40 molecule of a dendritic cell. Some pharmaceuticals of the present invention are formulated with an adjuvant and others are free. Desirable embodiments also comprise the ligand in a support-bound form. Optionally, the superactivation modulating agents are provided in an aggregated form as created, for example, by heating.

In another method, a ligand selected for its ability to block, inhibit, or prevent the activation of a killer T cell by virtue of an interaction with an APC is incorporated into a pharmaceutical. Accordingly, a ligand which interacts with an APC, desirably a dendritic cell, and thereby blocks, inhibits, or prevents superactivation of the APC or activation of a T cell is selected and incorporated into a pharmaceutical by conventional techniques. Preferable ligands include, but are not limited to, 17A10, 2D10, CTLA-4-Ig, MR1, CD40 5C3, Mab-89, BE-1, EA5, and M3 and fragments or derivatives thereof. Other embodiments include a soluble, non-aggregated form of anti-CD40 or of anti-CD40 ligand. Further, ligands which interact with CD40 by, for example, competitively inhibiting the binding of molecules which superactivate an APC through CD40 are embodiments. A novel class of inhibitors which bind the CD40 receptor or its ligand with high avidity but fail to superactivate the APC are designed using approaches in rational drug design, described above. Some pharmaceuticals are formulated in adjuvant and others are free or are provided in the form of a support-bound agent. As above, an aggregated form of this aspect is created by heating the proteins and is administered to subjects in need.

Although there may be many other methods of obtaining a pharmaceutical comprising a ligand which interacts with a CD40 molecule of an APC and thereby superactivates the APC or which interacts with an APC and thereby blocks, inhibits, or prevents activation of a killer T cell, we contemplate that a pharmaceutical obtainable by the methods described above are within the scope of embodiments of the present invention. Notably, many routes may be taken to arrive at the pharmaceutical product of the processes described above, however, the products remain identical or equivalent in so far as their ability to superactivate an APC by interacting with a CD40 molecule or block, inhibit, or prevent activation of a killer T cell by interacting with an APC.

The pharmaceutical products obtainable by the methods detailed in this dislcosure are useful for the treatment and prevention of cancer, infections, and autoimmune responses. By one approach the ligands identified as potentiating a superactivating state in an APC are selected as a cancer or anti-pathogen vaccine component. Additionally, some embodiments of cancer and anti-pathogen vaccine components comprise ligands identified for their ability to inhibit the superactivation of an APC. One method of making a cancer or anti-pathogen vaccine component includes contacting an APC, preferably a dendritic cell, with a ligand which interacts with the APC and thereby superactivates the APC. The activation state of several ligands are analyzed using the approaches detailed above and the superactivating ligands are incorporated into a pharmaceuticals as vaccine components. Preferable components for a cancer or anti-pathogen vaccine include, but are not limited to, the soluble, non-aggregated forms of antibodies which directly or indirectly interact with CD40, such as FGK45, HM40-3, 3/23, 5C3, Mab-89, BE-1, EA5, and M3 and fragments or derivatives thereof and antibodies which interact with a CD40 ligand. In some embodiments, vaccine components are formulated in adjuvant and, in others, the vaccine components are free. Desirably, the vaccine components are provided in the form of a support-bound agent.

The manufacture of a component for immunosuppression is another embodiment of the present invention. By one method, an APC, preferably a dendritic cell, is contacted with a ligand which interacts with the APC and the activation state of the APC is analyzed by the superactivation assays presented above. Ligands for use as the component for an immunosuppression agent are then selected based on the ability of the ligand to block, inhibit, or prevent killer T cell activation by interacting with the APC. Selected ligands are incorporated into pharmaceuticals and are administered to subjects in need. Preferable components for immunosuppression agents include, but are not limited to, the soluble, non-aggregated forms of antibodies against a CD40 ligand plus 17A10, 2D10, CTLA-4-Ig, and MR1 and fragments or derivatives thereof. In some embodiments, the immunosuppression component is formulated in adjuvant and in other embodiments the immunosuppression component is free. Desirably, the immunosuppression component is provided in the form of a support-bound agent.

Additionally, therapeutic and prophylactic agents which comprise superactivated APCs are embodiments of the present invention. In this aspect, for example, an APC, preferably a dendritic cell, is obtained from a subject in need of treatment or prophylaxis for cancer or infection by a pathogen. The APC is contacted with a cancer cell antigen and the contact results in the formation of an antigen-APC complex. The antigen-APC complex is then contacted with a ligand which superactivates the APC resulting in the formation of a superactivated antigen-APC complex. A therapeutically effective amount of the superactivated antigen-APC complex is administered to the subject so as to treat or prevent cancer or infection by a pathogen. Preferable superactivating ligands include, but are not limited to, FGK45, HM40-3, 3/23, 5C3, Mab-89, BE-1, EA5, and M3 and fragments or derivatives thereof, as well as, antibodies which interact with a CD40 ligand. Methods of immunotherapy of cancer comprising administration of dendritic cells are known in the art and these techniques are readily adapted for the delivery of superactivated dendritic cells to treat cancer or infection by a pathogen given the present disclosure. (See e.g., Gilboa et al., *Cancer Immunol. And Immunoth.* 46:82–87 (1998), herein incorporated by reference).

The pharmacologically active compounds of this invention are processed in accordance with conventional methods of galenic pharmacy to produce medicinal agents for administration to subjects, e.g., vertebrates including humans. The superactivation modulating agents are incorporated into pharmaceutical products with and/or without modification. Further, pharmaceuticals and/or therapeutic agents which deliver the superactivation modulating agent or a nucleic acid sequence encoding the superactivation modulating agent by several routes are manufactures of the present invention. For example, and not by way of limitation, some embodiments use of DNA, RNA, and viral vectors having sequence encoding the superactivation modulating agent. Nucleic acids encoding a desired superactivation modulating agent are administered alone or in combination with peptides or the ligand protein.

In some aspects, the compounds of this invention are employed in admixture with conventional excipients, i.e., pharmaceutically acceptable organic or inorganic carrier substances suitable for parenteral, enteral (e.g., oral) or topical application which do not deleteriously react with the active compounds. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations are, preferably sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

In the following disclosure, doses and methods of administration of a superactivation modulating agent are provided.

Dosage and Methods of Administration

The effective dose and method of administration of a particular formulation of a superactivation modulating agent varies based on the individual subject and the stage of the disease, as well as other factors known to those of skill in the art. Therapeutic efficacy and toxicity of such compounds is determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the superactivation modulating agent or to maintain the state of superactivation of an APC or inhibition of an APC. Additional factors which may be taken into account include the severity of the disease state, age, weight, and gender of the patient; diet, time and frequency of administration, drug combination(s), reaction sensitivities, and tolerance/response to therapy. Long acting pharmaceutical compositions are administered every 3 to 4 days, every week, or once every two weeks depending on half-life and clearance rate of the particular formulation.

Normal dosage amounts of superactivation modulating agent vary from 0.1 to 100,000 micrograms, up to a total dose of about 10 grams, depending upon the route of administration. Guidance as to particular dosages and methods of delivery is provided in the literature. (See U.S. Pat. Nos. 4,657,760; 5,206,344; or 5,225,212.) More specifically, the dosage of the superactivation modulating agent of the present invention is one that provides sufficient agent to attain superactivation of an APC or inhibition of superactivation of an APC. A constant infusion of a superactivation modulating agent is also provided in some embodiments so as to maintain a stable concentration in the tissues as measured by blood levels.

Routes of administration of the superactivation modulating agents include, but are not limited to, topical, transdermal, parenteral, gastrointestinal, transbronchial, and transalveolar. Topical administration is accomplished via a topically applied cream, gel, rinse, etc. containing a peptide agent. Transdermal administration is accomplished by application of a cream, rinse, gel, etc. capable of allowing the peptide agent to penetrate the skin and enter the blood stream. Parenteral routes of administration include, but are not limited to, electrical or direct injection such as direct injection into a central venous line, intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally.

Compositions of superactivation modulating agent-containing compounds suitable for topical application include, but not limited to, physiologically acceptable implants, ointments, creams, rinses, and gels. Any liquid, gel, or solid, pharmaceutically acceptable base in which the superactivation modulating agents are at least minimally soluble is suitable for topical use in aspects of the present invention. For topical application, there are also employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

Compositions of the superactivation modulating agents suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al.

Compositions of the superactivation modulating agents suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, or subcutaneous injection of the peptides. Additional embodiments for parenteral application include injectable, sterile, oily solutions, suspensions, emulsions, or implants, including suppositories. Ampoules are convenient unit dosages.

Compositions of the superactivation modulating agents suitable for transbronchial and transalveolar administration include, but are not limited to, various types of aerosols for inhalation. Devices suitable for transbronchial and transalveolar administration of the superactivation modulating agents are also embodiments. Such devices include, but are not limited to, atomizers and vaporizers. Many forms of currently available atomizers and vaporizers can be readily adapted to deliver superactivation modulating agents.

Compositions of the superactivation modulating agents suitable for gastrointestinal administration include, but not limited to, pharmaceutically acceptable powders, tablets, pills, dragees, capsules, drops, or liquids for ingestion and suppositories for rectal administration. A syrup, elixir, or the like can be used wherein a sweetened vehicle is employed.

Sustained, pro-drugs, or directed release compositions are also formulations used in embodiments of the present invention, e.g., liposomes or those wherein the active compound is protected with differentially degradable coatings, e.g., by microencapsulation, multiple coatings, etc. It is also possible to freeze-dry the ligands and use the lyophilizates obtained, for example, for the preparation of products for injection.

Aspects of the invention also include a coating for medical equipment. For example, in some embodiments the superactivation modulating agents are impregnated into a polymeric medical device such as catheters, stents and prosthetics. Coatings suitable for use in medical devices are provided by a powder containing the superactivation modulating agents or by polymeric coating into which the superactivation modulating agents are suspended. Suitable polymeric materials for coatings or devices are those which are physiologically acceptable and through which a therapeutically effective amount of a superactivation modulating agent can diffuse. Suitable polymers include, but are not limited to, polyurethane, polymethacrylate, polyamide, polyester, polyethylene, polypropylene, polystyrene, polytetrafluoroethylene, polyvinyl-chloride, cellulose acetate, silicone elastomers, collagen, silk, etc. Such coatings are described, for instance, in U.S. Pat. No. 4,612,337, issued Sep. 16, 1986 to Fox et al. which is incorporated herein by reference.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

The example below discloses the materials and methods used to perform the experiments described above. The materials and methods and the experiments presented above are also detailed in Ridge et al., *Nature* 393: 474 (1998), herein incorporated by reference.

EXAMPLE 1

Mice and Immunizations

C57B1/6 (B6) female and male mice were purchased from Taconic farms Germantown N.Y. MHC class II knock-out mice (KO) were obtained from the NIAID mouse breeding contract (Taconic Farms Inc. Germantown N.Y.). The KO mice were bred onto both the C57B1/6 and C57B1/10 background to N13 and N11 respectively. Both types of mice were used in this study. The mice were left unprimed or were primed to the male antigen, H-Y, by an intraperitoneal injection of $3 \times 10^6$ male spleen cells in 200 µl of sterile phosphate buffered saline (PBS). Mice primed with dendritic cells (see below) were given $5 \times 10^5$ cells in 200 µl PBS per mouse intraperitoneally. Some mice received a second injection of the original stimulating cells two weeks after the first injection.

CD4 Purification

Two weeks to 1 year after in vivo priming, spleens were removed from the responders and depleted for CD4 T cells using the Midi MACs system (Miltenyi Biotec, Germany) with MACS magnetic beads conjugated to the anti-mouse CD4 monoclonal antibody, GK1.5. By FACS analysis with the non-competing anti-CD4 antibody RM4-4 (Pharmingen, San Diego, Calif.), the depleted populations routinely contained less than 0.2% CD4 cells.

Dendritic Cells

The enriched dendritic cell preparations were obtained by incubating B6 male spleen cells in Iscove's Modified Dulbecco's Medium (IMDM) plus 10% fetal calf serum, $5 \times 10^{-5}$ M 2-mercaptoethanol, glutamine, penn-strep and gentomycin (complete medium) in Falcon tissue culture dishes #3025 for 2 hours at 37° C., removing nonadherent cells and incubating the remaining adherent cells overnight at 37° C. in medium containing 2 ng/ml mouse recombinant granulocyte-macrophage colony stimulating factor (rGM-CSF) and 200 U/ml recombinant mouse IL-4 (Pharmigen). Nonadherent cells were then harvested and further purified over a 50% Percoll density gradient.

CD40 Cross-linking

The enriched dendritic cells were incubated in PBS plus 10% mouse serum for 10 min on ice, then washed once with cold PBS. They were then incubated for 20 mins on ice, mixing occasionally, with a Hamster anti mouse CD40 (HM40-3) or IgG2a Rat anti mouse CD40 (3/23) (Pharmigan) monoclonal antibodies at 5 µg/ml and 3.5 µg/ml respectively, and washed once in PBS. The cells were then incubated with either Goat anti Hamster or Goat anti Rat antibodies (Caltag, Burlingame Calif.) in complete medium containing 2 ng/ml GM-CSF and 200 U/ml IL4 and incubated overnight at 37° C. The cells were harvested the next day and either used as irradiated in vitro stimulators (1500 Rads) or as cells for in vivo priming. The dendritic cells used in vivo were washed 3 times in sterile PBS before injection.

Infection with Influenza

Dendritic cells were infected with Influenza virus as described. (54). Briefly $10 \times 10^6$ or less male B6 or KO dendritic cells were resuspended in serum free medium with 1000 HAU of purified Influenza A/PR/8 for 90 mins at 37° C., mixing occasionally, then washed three times in complete medium. These cells were then irradiated (1500 Rads) and used as in vitro stimulators.

Stimulating with Marilyn

B6 dendritic cells were activated by incubating with Marilyn, a CD4 TH1 clone specific for H-Y and restricted by $A^b$ that was isolated from a B6×CBA/N female mouse (MHC bxk). $1 \times 10^6$ male dendritic cells were incubated overnight with $1.5 \times 10^5$ Marilyn. In some experiments, the mixture of dendritic cells plus Marilyn was then irradiated 1500 Rads and used as in vitro stimulators. In others, we removed the Marilyns, by FACS sorting with an antibody against $H-2^k$, before irradiating and adding the dendritic cells to the cultures. We tested for the efficiency of T cell removal by staining for CD4, Thy1 and TCR, and by culturing an aliquot of the (unirradiated) dendritic cell populations and testing for proliferation. In every case, we found no evidence of contaminating Marilyn cells.

In vitro Cultures

Two weeks or later after the last in vivo immunization, $4 \times 10^6$ spleen cells were restimulated in 2 ml cultures with $2 \times 10^6$ irradiated B6 male spleen cells or $1.5 \times 10^5$ of the various populations of dendritic cells, with or with out an exogenous source of mouse IL-2, (10% Rat Con A supernatant, from which the ConA has been removed, Collaborative Biomedical Products, Bedford Mass.). Six days later the cultures were tested for their ability to kill male and female targets using the JAM Test. (55).

Antibody Blocking Cultures

Soluble antibody was titrated ½ starting at 500 or 300 µg/ml in 100 µl volumes using a 96 well round bottomed plate. 50 µl containing $1 \times 10^5$ unseparated or CD4 depleted spleen cells from a primed B6 female were added plus 50 µl containing $5 \times 10^4$ B6 (FIG. 4A) or MHC class II KO (FIG. 4B) male dendritic cells superactivated by CD40 crosslinking, to give a final volume of 200 µl in complete medium. Antibodies reported are Hamster anti-mouse B7.1 (17A10), Rat IgG2b anti-mouse B7.2, (2D10), recombinant mouse CTLA4/immunoglobulin fusion protein (CTLA4-Ig), and control antibodies Rat IgG2b anti-mouse Ly5.2 (A20.1.7) used in FIG. 4 with the B6 stimulators), and Rat Ig2b anti mouse MHC II (M5/114, used in FIG. 4 with the MHC KO stimulators). We also used Hamster antibody UC3 and human recombinant mouse CTLA4/immunoglobulin fusion protein (hu CTLA4-Ig) but they did not block and are not reported for the sake of clarity.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A method of identifying a ligand as a candidate for incorporation into a pharmaceutical composition comprising:

providing an antigen presenting cell (APC);

providing a candidate ligand which interacts with the APC;

contacting the APC with the candidate ligand;

analyzing the activation state of the APC; and selecting the ligand as the candidate for incorporation into the pharmaceutical wherein the ligand superactivates the APC, as determined by the capacity to activate a killer T cell in the absence of a helper T cell.

2. The method of claim 1, wherein the ligand is an anti-CD40 antibody.

3. The method of claim 1, wherein the composition is formulated in adjuvant or free.

4. The method of claim 1, wherein the APC is a dendritic cell.

5. The method of claim 1 wherein the ligand is provided in the form of a support-bound agent.

6. The method of claim 1, wherein the ligand interacts with CD40.

* * * * *